United States Patent [19]  [11] 4,076,028
Simmons  [45] Feb. 28, 1978

[54] FORCEPS SPACING DEVICE
[75] Inventor: Raymond W. Simmons, Pinellas Park, Fla.
[73] Assignee: Concept Inc., Clearwater, Fla.
[21] Appl. No.: 730,613
[22] Filed: Oct. 7, 1976
[51] Int. Cl.² .................. A61B 17/36; A61N 3/06
[52] U.S. Cl. .................. 128/303.13; 128/303.17; 174/88 R; 219/234; 339/247
[58] Field of Search .............. 128/303.13, 303.14, 128/303.15, 303.16, 303.17, 303.18, 405; 219/234, 90; 174/88 R, 88 S; 339/241, 247

[56] References Cited
U.S. PATENT DOCUMENTS

| 1,071,978 | 9/1913 | White | 128/303.13 |
| 2,012,937 | 9/1935 | Bevoy | 128/303.14 X |
| 2,636,971 | 4/1953 | Delbrook | 219/90 X |
| 3,249,908 | 5/1966 | Fuller et al. | 339/247 X |
| 3,643,663 | 2/1972 | Sutter | 128/303.17 |
| 4,041,952 | 8/1977 | Morrison, Jr. et al. | 128/303.13 |

Primary Examiner—Robert W. Michell
Assistant Examiner—Lee S. Cohen
Attorney, Agent, or Firm—Gipple & Hale

[57] ABSTRACT

An electrosurgical forceps comprising two blades which are electrically connected to an electrosurgical frequency generator so that electrosurgical radio frequencies can be transmitted from the generator to the blades. The blades are separated by a spacer member formed with a middle section defining inwardly inclined surfaces which hold the wires in a secured position against the forceps blades away from each other. The wire ends are bent down in channels formed in the spacer element and an elastomeric tubing is shrink fit around the ends of the blades to secure the spacer element and non-insulated wire ends in a fixed position.

12 Claims, 8 Drawing Figures

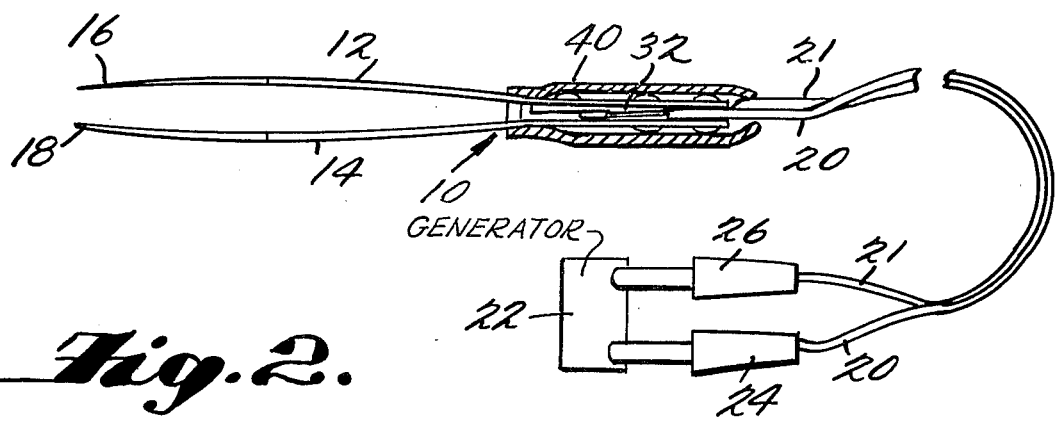
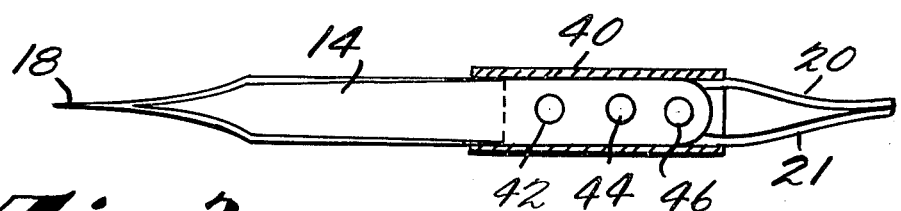
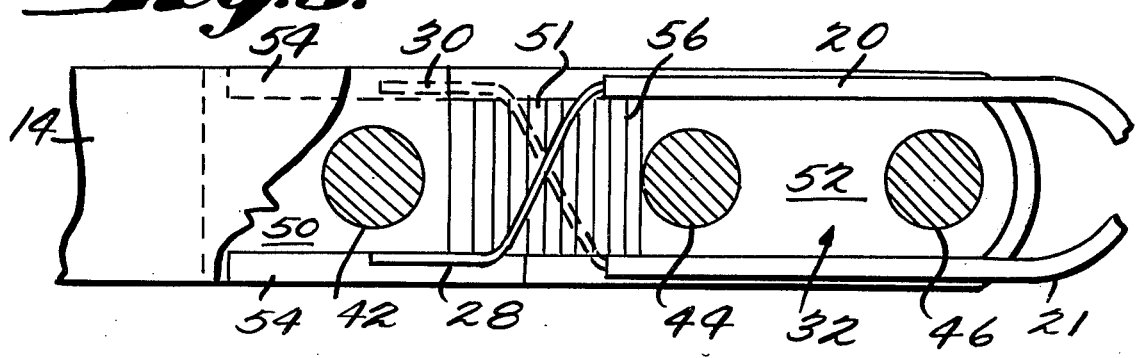
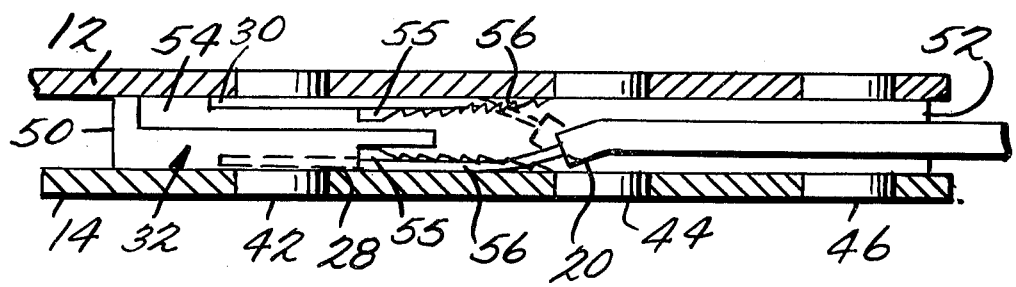

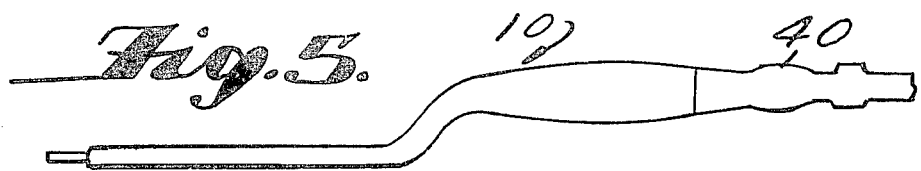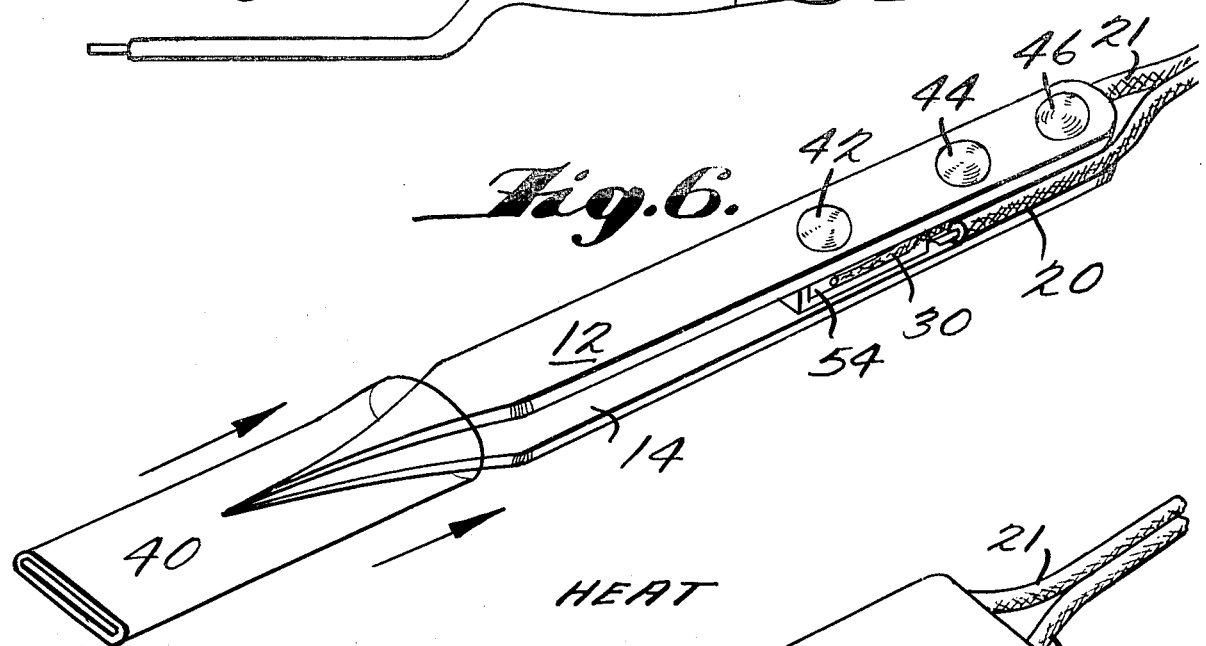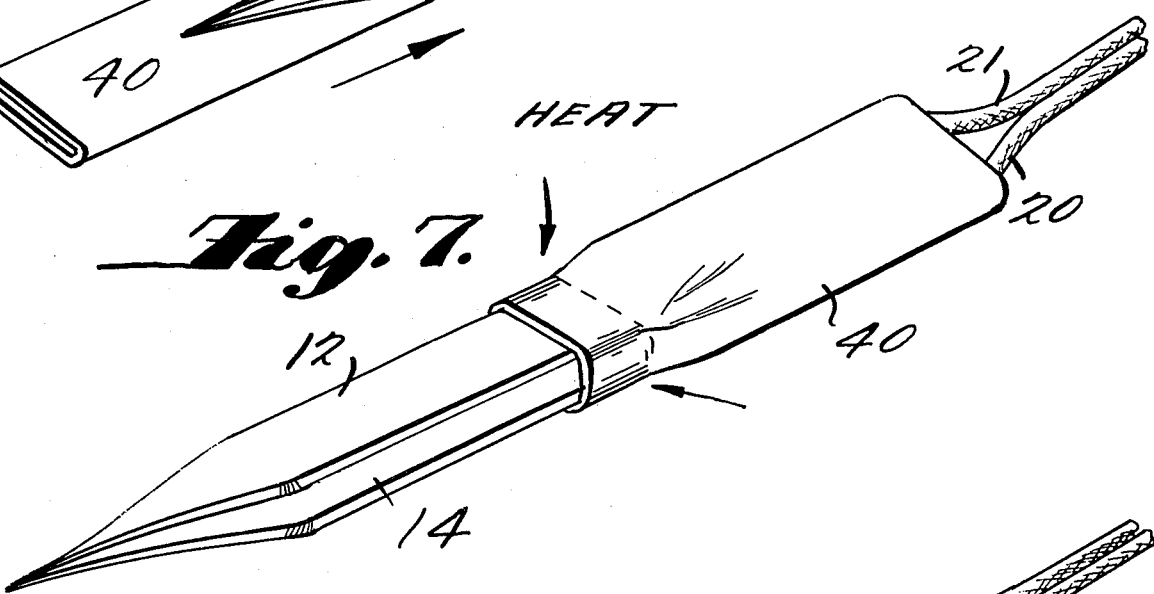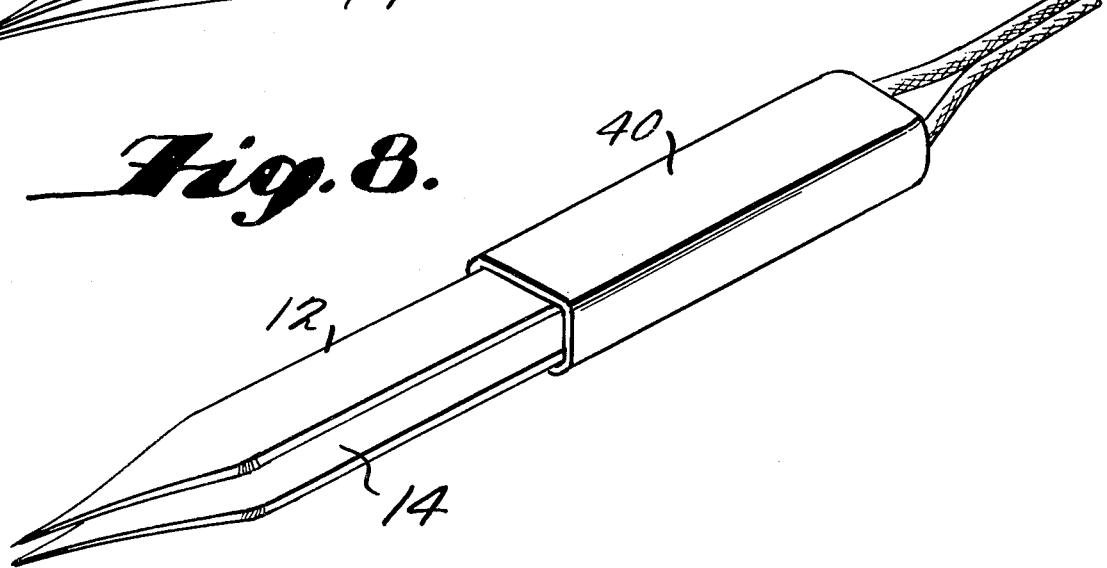

FORCEPS SPACING DEVICE

BACKGROUND OF THE INVENTION

This invention relates to coagulating instruments, and more specifically to a coagulating instrument of the forceps or tweezer type comprising means for electrically connecting the blades of the forceps to a generator supplying high frequency voltage for the purpose of coagulating tissue held between the points of the blades of the forceps. A locking plastic spacer member is provided between the blades of the forceps which serves to retain each uninsulated wire end in direct contact with only one of the blades of the forceps. The locking spacer member is held in place by means of an elastic tube which is shrink fit over the rear or fulcrum point of the forceps, thereby concealing the locking and spacing insert.

DESCRIPTION OF THE PRIOR ART

It is known in the prior art to have a forceps type coagulating instrument with a spacer separating the blades.

In such instruments the electrical connections are held on the blades by ears, pivot pins, rivets, screws, adhesive and other more complex fastening apparatus.

U.S. Pat. No. 3,643,663 discloses a forceps type coagulating instrument which is provided with means for electrically connecting the relatively insulated blades of a forceps to a generator supplying a high frequency voltage. When the high frequency voltage is supplied, any tissue held between the blades of the forceps will be coagulated. The principle feature of this forceps type coagulating instrument consists in the fact that the high-frequency voltage is supplied to the coagulating forceps through a push-on and pull off connector. The rear ends of the forceps blades are connected together with an insulating insertion held therebetween. This rear end assembly is then inserted into the spring assembly of the connector and held therein by the clamping springs of the spring assembly.

U.S. Pat. No. 3,831,607 discloses an electrocoagulation grasping forceps for tube sterilization utilizing a bi-polar high-frequency heat radiation. The particular advantage of this coagulation forceps lies in the fact that only that part of the tissue which must be eliminated is seized and exposed to heat radiation, so that any other part of the tissue cannot be destroyed or damaged. The grip sections have only an external insulation and therefore only that part of the tissue lying in the interior of the closed grip section can be exposed to heat radiation.

U.S. Pat. No. 3,100,489 discloses a radio frequency cauterizing apparatus in which an insulated electrocoagulation forceps is provided with a built-in control switch which is automatically operative from the surgeon's hands through a relay controlled unit. The operating surgeon grasps the tissue to be cauterized between the exposed tips of the forceps and exerts a slight additional amount of pressure required to bring the electrical contacts together in order to close the control switch and complete the control circuit.

The wire conductors connect the relay control point to the forceps. One wire conductor is connected in direct electrical contact with the forceps and a switch element positioned on the inside of one of the forceps arms electrically integral with the forceps. The other conductor from the relay box is connected in electrical contact with a switch contact element disposed on the inner surface of the other arm of the forceps but electrically insulated from the forceps.

Other United States Patents of interest are U.S. Pat. Nos. 371,664 and 1,586,645 which disclose electrical forceps for treating or coagulating animal tissue and U.S. Pat. No. 1,908,201 which discloses a bi-polar tonsil/forceps.

SUMMARY OF THE INVENTION

It is a common practice in some surgical techniques to use electro-surgical frequency current for the cauterization or electro-coagulation of small blood vessels. Due to the extreme delicacy of the surgical technique, a compact, simple and easy to manipulate hand held tool is not only desirable, but an essential requirement for efficient and mistake-proof surgery. Electrical forceps or tweezers are old in the art, and are generally bulky, subject to breakage, and relatively expensive to assemble. One of the major costs involved in the manufacture and assembly of a pair of electrical tweezers or forceps resides in the connection of the blades of the forceps with the electrical wires which are directly connected to the electrosurgical generator. It is a safety requirement that the electrical contacts be held directly in contact with the forceps blades and in a completely immobile manner. If either one of the electrical wires is not held in contact with the blades of the forceps, possible grounding or shorting may occur, to the ultimate detriment of the patient or surgeon.

The present invention comprises a pair of electrosurgical forceps or tweezers in which the electrical wires connecting the electrosurgical generator to the blades of the forceps are held in place by an inexpensive plastic spacer which serves to keep the ends of the wire leads separate from one another and in direct contact with the blades of the forceps. The spacer is a molded plastic part designed to allow the electrical wire contacts to be self locking. The wire contacts when placed on the inclined surface of the spacer over the serrated edges of the spacer are locked into place when pulled, thus producing a stable inexpensive relatively non-destructable surgical instrument. Not only is the plastic spacer relatively inexpensive but the production costs due to the utilization of the spacer are greatly diminished and consequently electrosurgical forceps can be manufactured at a much lower cost than those presently available.

An elastomeric tubular sleeve is slipped over the rear end of the blades of the forceps and shrink fit in order to hold the spacer member in place and out of sight between the blades of the forceps to provide maximum contact between the interior edges of the blades of the forceps and the electrical wire contacts.

The above mentioned purposes are more readily apparent when read in conjunction with the following detailed description of a preferred embodiment of the present invention.

BRIEF DESCRIPTION OF THE DRAWINGS

FIG. 1 is a top plan view of the forceps apparatus of the present invention partially in section, FIG. 2 is a side elevational view of the forceps of FIG. 1 with the shrink tubing removed, FIG. 3 is an enlarged side elevational view of the rear end of the forceps shown in FIG. 1 partially in section showing the spacer member;

FIG. 4 is a top plan view of the section of forceps shown in FIG. 3,

FIG. 5 is an alternate side elevational view of a bayonette embodiment of the forceps invention, FIG. 6 is a perspective view of the forceps invention showing the heat tube placed on the tip of the forceps, FIG. 7 is a view of FIG. 6 with the heat shrink tube placed over the end of the forceps invention; and FIG. 8 is a perspective view of the forceps invention with the heat shrink tube shrink fit over one end of the forceps.

DETAILED DESCRIPTION OF THE DRAWINGS

As is shown by the drawings, a forceps or bayonet tweezer 10 with blades 12 and 14 forming pointed ends 16, 18, respectively, is connected via electrical wires 20 and 21 to an electrosurgical frequency generator 22. Male connecting plugs 24 and 26, are utilized to connect the electrosurgical generator 22 to the electrical wires 20 and 21. The electrical wires 20 and 21 have two electrical contact ends 28 and 30, which serve to electrically connect the blades 12 and 14, of the forceps 10 to the electrical wires 20 and 21. These electrical contact ends 28 and 30 are held firmly against the blades 12 and 14 of the forceps by means of an inclined plastic spacer member 32. The electrical contact ends 28 and 30 of the electrical wires 20 and 21 are formed by removing a portion of the insulating material from the wires. As best seen in FIG. 3, with the elastomeric tubular sleeve 40 removed, the two ends 28 and 30 of the electrical wires 20 and 21 are stripped of their insulating material. One contact 28 of the electrical wire 20 is held against blade 12 while the other electrical contact 30 is held firmly against the blade 14. The plastic spacer member 32 is held firmly between the rear end of the forceps or bayonet tweezers blades 12 and 14 by three plastic rivets 42, 44 and 46.

The plastic spacer member 32 is constructed of a polycarbonate material and serves as an insulator, consequently preventing any contact between the non-insulated ends of the electrical contacts 28 and 30 or the rear ends of the tweezer blades 12 and 14. The plastic spacer member 32 has a forward section 50, a middle section 51 and a rear section 52.

The forward section 50 has a rectangular configuration and serves to space the blades 12 and 14 apart from each other and hold the bare wire ends 28 and 30 apart from each other. Similarly, rear section 52 is rectangular in shape and serves to space the rear most portions of the blades 12 and 14 apart. The width of the forward section 50 is equal to the width of the tweezer blades. Channels 54 are cut in the sides of the forward sectin 50 and serve to hold wire ends 28 and 30. The width of the rear section 52 is less than the width of the blades by an amount equal to the thickness of the two insulated electric wires 20 and 21. The plastic spacer member 32 additionally is formed with a middle section 51 which serves to hold securely the uninsulated ends of the electrical contacts 28 and 30 against the interior edges of the blades 12 and 14. The middle section 51 of the plastic spacer member has two inclined surfaces 56 extending generally from the first rivet 42 to the second rivet 44. The rivets 42 and 44 are located at the points at which the blades 12 and 14 are fastened with the plastic spacer member 32 held securely therebetween. The thickness of the middle section 51 of the plastic insert 32 is smallest at the point nearest the first rivet 42, while the thickness of the middle section 51 is greatest at the point proximate to the second rivet 44. The thickness of the middle section 51 gradually increases from the first rivet at which the thickness is smallest, by angular step-like increments on both inclined surfaces which steps take serrated or jagged toothlike configuration. A third plastic rivet 46 is also provided at the rear of the blades 12 and 14 of the forceps or bayonet tweezers 10 in order to secure the plastic spacer between the blades.

As the middle section 51 has a thickness less than the thickness of the forward or rear sections 50 and 52, respectively, two wire insertion apertures 55 are formed in the area between the blades and the middle section 51 of the plastic spacer member.

An elastomeric tubular envelope 40 is provided which is shrink fitted over the rear end of the blades 12 and 14, i.e., completely covering the three rivets. The shrink fit envelope creates pressure on the rear end of the forceps and serves to hold the blades 12 and 14 of the forceps flush against the plastic spacer member so that the inclined surface of the middle section securely holds the electrical contacts 28 and 30.

In order to manufacture the surgical tweezers in an efficient and economical way, the plastic spacer member is first riveted between the forceps blades.

The ends of the electrical contacts 28 and 30 of the electrical wires 20 and 21 are then inserted, from opposite sides, into the wire insertion apertures 55. The insulated portions of the electrical wires 20 and 21 lie flush against the sides of the rear section 52. In this way the electrical wires do not extend over the sides of the tweezer blades. The exposed ends of the electrical contacts 28 and 30 extend through the opposite sides of the wire insertion apertures 55 and the electrical wires 20 and 21 are pulled rearwardly with respect to the forceps blades, thereby securing the wire contacts between the inclined serrated surfaces 56 and the forceps or tweezer blades. Subsequently, the bare wire ends 28 and 30 are bent forward into the oppositely positioned channels 54 each of which is adjacent to its respective blade. Thus it can be seen that the plastic insert serves as an efficient means to securely install the contact wires in addition to its function of prohibiting the electrical contacts from contacting each other.

While the preferred embodiment of the invention has been disclosed, it is understood that the invention is not limited to such an embodiment since it may be otherwise embodied in the scope of the appended claims.

What is claimed is:

1. An electrosurgical forceps comprising two electrically conductive blades each blade having a forward end and a rear end, an electrosurgical frequency carrying insulated wire means for connecting only said forceps blades to an electrosurgical frequency generator, said wire means being secured to said forceps blades and adapted to be connected to said generator, a spacer means constructed of insulative material secured between the rear ends of said blades, said spacer means comprising a front section and a rear section, both sections conforming to the shape of the forceps blades and a middle section defining two inclined serrated surfaces extending between the front section and rear section, said inclined serrated surfaces engaging said wire means to secure the wire means against said forceps blades in direct electrical contact with each of the forceps blades.

2. An electrosurgical forceps as claimed in claim 1 wherein said spacer means is constructed of a plastic insulating material.

3. An electrosurgical forceps as claimed in claim 1 wherein said spacer means defines channel means on each opposite side adjacent the nearest blade for holding said wire means.

4. An electrosurgical forceps as claimed in claim 1 wherein said wire means comprises two wires ecch having a non-insulated end secured to a blade and said spacer means separates the non-insulated ends of said wires and prevents them from contacting each other.

5. An electrosurgical forceps as claimed in claim 1 wherein the spacer means and rear ends of the forceps blades are covered by an elastomeric tubing.

6. An electrosurgical forceps as claimed in claim 5 wherein the elastomeric tubing is shrink fit around the rear ends of the forceps blades and said spacer means.

7. An electrosurgical forceps comprising two tweezer shaped electrically conductive blades, an electrosurgical frequency carrying insulated wire means having two uninsulated ends adapted to connect said tweezer blades to an electrosurgical frequency generator, a wire connecting means for connecting said ends to each of the blades of said forceps while precluding the wire ends from contacting each other, said wire connecting means comprising a molded insulative spacer element secured between the blades and defining a body having a front section, a rear section and a middle section, the middle section being formed with inclined surfaces engaging the uninsulated ends of said wire means to hold the uninsulated ends in a secured position in contact with the forceps blades when the ends are secured to the inclined surfaces.

8. An electrosurgical forceps as claimed in claim 7 wherein said spacer element is polycarbonate plastic.

9. An electrosurgical forceps as claimed in claim 7 wherein said inclined surfaces are formed with incremental angular steps.

10. An electrosurgical forceps as claimed in claim 9 including a shrink material covering shrink fit over said spacer element and at least a portion of said blades.

11. An electrosurgical forceps as claimed in claim 7 including rivet means projecting from said spacer element body secured to said blades.

12. An electrosurgical forceps as claimed in claim 7 wherein said tweezer shaped blades are bayonette shaped.

* * * * *